United States Patent
Lundberg

[11] Patent Number: 6,126,625
[45] Date of Patent: Oct. 3, 2000

[54] ORTHOTIC DEVICE FOR A JOINT OF THE HUMAN BODY

[76] Inventor: Leslie C. Lundberg, 303 Dublin Cir., Smithville, Mo. 64089

[21] Appl. No.: 08/820,596

[22] Filed: Mar. 19, 1997

[51] Int. Cl.$^7$ .................................................. A61F 5/00
[52] U.S. Cl. .................................................. 602/27; 602/65
[58] Field of Search ................................. 602/5, 20, 21, 602/23, 27–29, 60, 61, 62, 65

[56] References Cited

U.S. PATENT DOCUMENTS

| | | | |
|---|---|---|---|
| 459,616 | 9/1891 | Von Rohonczy | 602/27 |
| 1,058,322 | 4/1913 | Mueller | 602/27 |
| 1,374,669 | 4/1921 | McClellan | 602/27 |
| 1,666,290 | 4/1928 | Johnston . | |
| 3,073,305 | 1/1963 | Biggs, Jr. et al. | 602/27 |
| 3,970,083 | 7/1976 | Carrigan . | |
| 4,187,844 | 2/1980 | Caprio, Jr. . | |
| 4,280,488 | 7/1981 | Polsky et al. . | |
| 4,556,053 | 12/1985 | Irons . | |
| 4,556,054 | 12/1985 | Paulseth . | |
| 4,646,726 | 3/1987 | Westin et al. . | |
| 4,651,726 | 3/1987 | Holland . | |
| 4,753,229 | 6/1988 | Sutherland . | |
| 4,852,874 | 8/1989 | Sleichter, III et al. . | |
| 4,865,023 | 9/1989 | Craythorne et al. . | |
| 4,922,630 | 5/1990 | Robinson . | |
| 4,982,733 | 1/1991 | Broadhurst et al. . | |
| 5,014,690 | 5/1991 | Hepburn et al. . | |
| 5,016,623 | 5/1991 | Krahenbuhl | 602/27 |
| 5,050,620 | 9/1991 | Cooper . | |
| 5,088,478 | 2/1992 | Grim . | |
| 5,163,450 | 11/1992 | Cadichon et al. . | |
| 5,330,419 | 7/1994 | Toronto et al. . | |
| 5,437,611 | 8/1995 | Stern . | |
| 5,472,414 | 12/1995 | Detty | 602/27 |
| 5,700,237 | 12/1997 | Hess | 602/27 |

*Primary Examiner*—Kim M. Lee
*Attorney, Agent, or Firm*—Hovey, Williams, Timmons & Collins

[57] ABSTRACT

An orthotic device for a joint of the human body includes an elongated element having an elastic portion, and structure for mounting the element on the body in a mimicking relationship with one of the muscles and the associated tendons collectively extending across the joint. The structure is operable to secure the element to the body in such a manner that the element extends across the joint and is retained in the vicinity of the joint against substantially all movement other than linear extension and retraction.

53 Claims, 2 Drawing Sheets

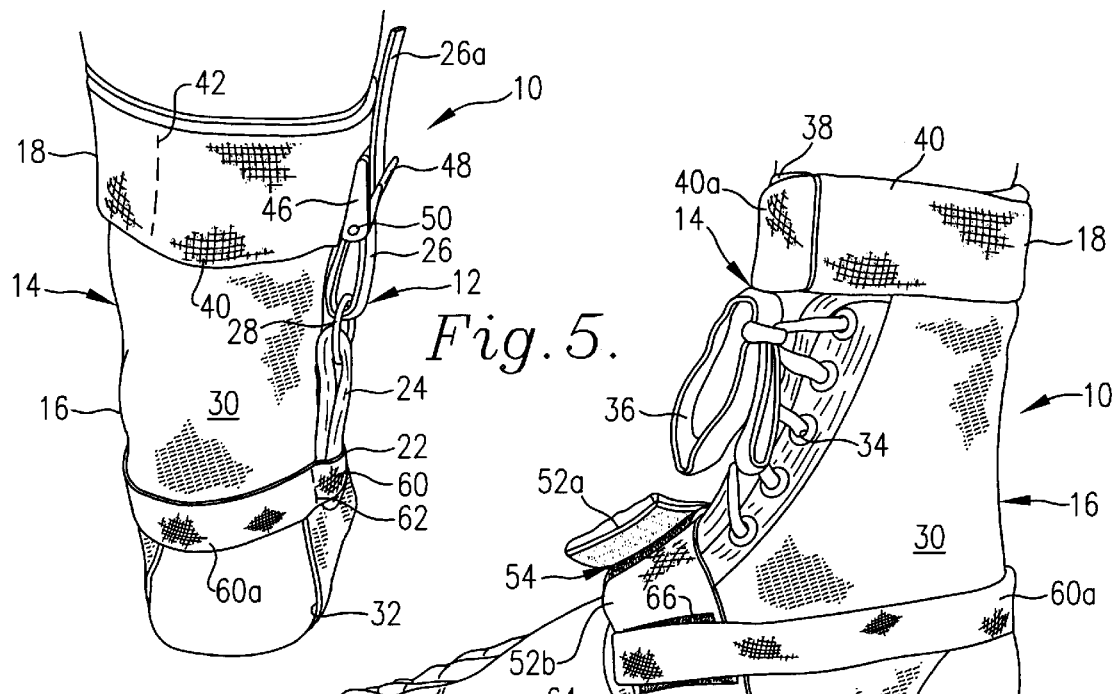
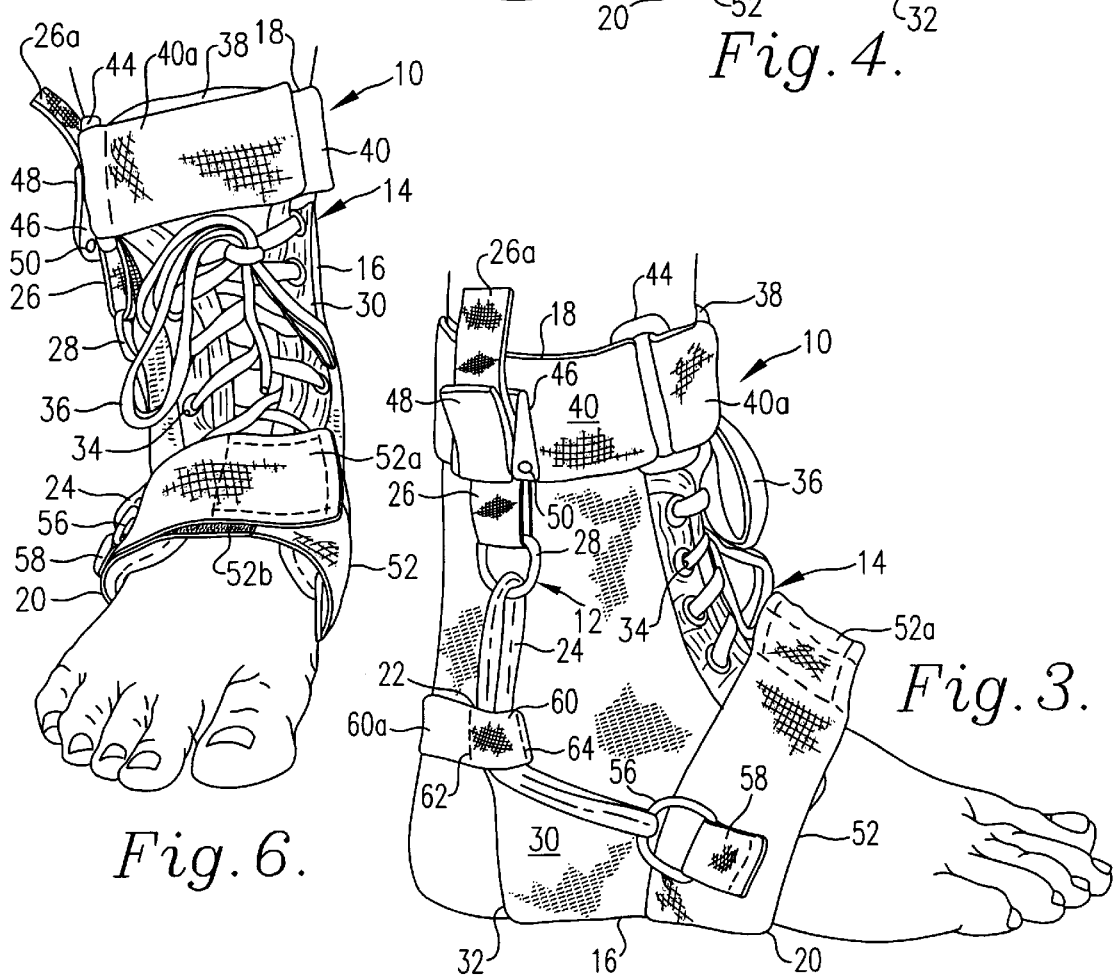

ORTHOTIC DEVICE FOR A JOINT OF THE HUMAN BODY

BACKGROUND OF THE INVENTION

1. Field of the Invention

The present invention relates generally to medical and surgical equipment and, more particularly, to an orthotic device for one of the joints of the human body, such as the ankle or wrist, wherein the device includes structure for mimicking one of the muscles and the associated tendons extending across the joint.

2. Discussion of the Prior Art

Treatment of a sprained joint often involves restricting flexation of the joint against movement in a direction which would further injure or place undue stress on the injured ligaments, muscles or tendons. Immobilization of the joint is commonly accomplished by placing a brace, having one or more rigid splints, on the joint. For example, in the case of a lateral sprain of the ankle joint, a traditional brace includes a pair of rigid splints disposed along the inner and outer sides of the lower leg and ankle joint for preventing inversion and eversion of the ankle joint (i.e., turning in and out of the foot, respectively). Similar to the ankle brace, a conventional brace for treating a wrist joint sprained due to excessive flexion (i.e., excessive turning of the hand downwardly) includes a rigid splint extending along the underside of the arm and onto the palm of the hand for bracing the hand in a "cocked up" position. Of course, this type of wrist brace prevents flexion of the wrist joint out of the "cocked up" position. The hand is typically secured to the splint by a bandage or cloth sleeve so that extension of the wrist joint (i.e., turning of the hand upwardly) is also prevented.

In any case, a "splint-type" brace is often useful during the acute stage of the injury because immobilization of a joint may be desired as the injured tissue initially begins to heal. However, this type of brace is typically bulky and therefore cannot be worn inside a shoe or clothing. Further, discomfort is often a problem with a "splint-type" brace, especially when the brace is tightened about the joint to reduce swelling. Another serious problem with a "splint-type" brace is that essentially all joint function is prevented, which restricts activity involving use of the joint and, more importantly, is undesirable during the rehabilitation stage of the injury. That is, it is desirable to progressively reduce the degree of immobilization of the joint during rehabilitation so that the injured muscle is strengthened as the joint is returned to normal activity. Moreover, immobilization of the joint may cause atrophy in both the injured and non-injured tissue. For example, if the extensor digitorum tendon is strained due to excessive flexion of the wrist joint and a "splint-type" brace, as described above, is used to immobilize the wrist joint, eccentric contraction of the extensor digitorum muscle and concentric contraction of the flexor digitorum, along with contraction of other muscles associated with the wrist, are prevented. The treatment afforded by the brace consequently does not focus only upon the injured tissue, and accordingly, joint function is overly restricted by the brace.

Wrapping of the joint with a cloth bandage or tape is another conventional technique for immobilizing a joint. Although cloth or tape wraps are more comfortable and less bulky than "splint-type" braces, the wraps likewise immobilize the joint and therefore present the same problems of atrophy, lack of performance during the rehabilitation stage of the injury, and excessive restriction of joint function. In fact, tape and cloth wraps are traditionally more restrictive than the "splint-type" braces because the wraps encircle the joint and adjacent body parts. For example, a "splint-type" ankle brace for lateral sprains of the ankle joint, as described above, sometimes allows limited dorsi and plantar flexion of the ankle joint. Cloth and tape wraps are also difficult and cumbersome to apply by the wearer and therefore often require assistance from another person, such as a trainer. Further, wrapping of the joint must be done carefully, otherwise the cloth or tape wrap may cut off circulation if wrapped too tightly or provide virtually no support if wrapped too loosely.

Braces have been designed for use during the rehabilitation stage of injuries. Rehabilitative braces typically include a pliable sleeve formed of elastic material for placement on the joint and adjacent body parts. For example, a rehabilitative ankle brace traditionally comprises a boot-shaped sleeve that is tightened about the lower leg, ankle joint and foot by suitable lacing. Although this type of brace is comfortable and capable of being worn within a shoe, the sleeve itself provides little support to the joint. Accordingly, the sleeve would not be effective during the acute stage of an injury because of its failure to sufficiently restrict movement of the joint. Even when the sleeve is used for rehabilitative purposes, it restricts movement of the joint in virtually any direction and consequently fails to focus only on the injured tissue. It will be appreciated that rehabilitative sleeves are also often used as a prophylaxis for reducing the risk of re-injury.

Rehabilitative sleeves have been provided with various structure in an attempt to broaden their application to include treatment during the acute stage of the injury. For example, sleeves have been provided with rigid splints inserted into pockets formed along the sleeve. However, this type of brace still presents the same problems noted above and still lacks sufficient versatility to have effective application during all stages of the injury. Other types of orthotic devices for use during the various stages of an injury have been developed. In general, however, multi-stage orthotics tend to have complex and expensive constructions and are difficult to install.

OBJECTS AND SUMMARY OF THE INVENTION

Responsive to these and other problems, an important object of the present invention is to provide a versatile orthotic device for a joint of the human body, which performs effectively during all stages of an injury and may also be used as a prophylaxis to reduce the risk of re-injury. Additionally, an object of the present invention is to provide an orthotic design that is useful on virtually any joint of the human body. It is also an object of the present invention to provide an orthotic device which may be used to exercise or rehabilitate the musculature associated with a joint. A further object of the present invention is to provide an orthotic device that is simple to use and relatively inexpensive to manufacture.

Another important object of the present invention is to provide an orthotic device having structure for mimicking one or more of the muscles and the associated tendons extending across the joint. A related object of the present invention is to provide such a device with a retainer that mimics the retinaculum associated with the joint for purposes which will be described below. Yet another object of the present invention is to provide an orthotic device with structure for preventing potentially injurious movements with minimal limitation to other non-injurious movements of the joint. In other words, one of the objects of the present invention is to provide an orthotic device which focuses on the injured tissue so that joint function is not overly restricted.

An additional important object of the present invention is to provide an orthotic device having the mimicking structure noted above, wherein the structure restricts extension of the mimicked muscle and supplements concentric contraction of the muscle. For example, an ankle orthotic would have mimicking structure for limiting inversion of the ankle joint to restrict extension of the peroneus brevis, and for biasing the ankle joint in an everted direction to supplement concentric contraction of the peroneus brevis. In this respect, another object of the present invention is to provide elastic mimicking structure, with the tension of the structure being adjustable to accommodate the various stages of the injury. For example, a wrist orthotic could include structure for mimicking both the extensor digitorum and the flexor digitorum muscles and tendons so as to restrict flexion and/or extension of the wrist joint, if necessary.

According to these and other objects apparent from the following description of the preferred embodiments, the present invention concerns an orthotic device for a joint of the human body, wherein the device includes an elongated element having an elastic portion, and structure for mounting the element on the body in a mimicking relationship with one of the muscles and the associated tendons collectively extending across the joint. The structure is operable to secure the element to the body in such a manner that the element extends across the joint and is retained in the vicinity of the joint against movement other than linear extension and retraction.

The element is consequently limited to movement which corresponds to movement of the mimicked muscle and tendons. That is, extension of the element corresponds substantially to movement of the mimicked muscle and tendons during eccentric contraction of the muscle, and retraction of the element corresponds substantially to movement of the mimicked muscle and tendons during concentric contraction of the muscle. Accordingly, the elastic portion of the element may be significantly tensioned so that the movement of the mimicked muscle and tendons corresponding to eccentric contraction of the muscle is prevented. Such an arrangement may be useful during the acute stage of an injury to the mimicked muscle or tendons. The tension of the elastic portion is preferably adjustable so that the device may also be used during rehabilitation of the injured tissue. For example, the elastic portion may be slightly stretched when the joint is in a neutral position so that movement of the joint in a direction corresponding to eccentric contraction of the mimicked muscle is limited, and the joint is biased in a direction corresponding to concentric contraction of the muscle. Thus, the mimicked muscle and tendons are not unduly stressed during movement corresponding to concentric and eccentric contraction of the muscle.

When the device is used as a prophylaxis, the elastic portion of the element is preferably under slight tension when the joint is in a neutral position so as to urge the joint in a direction corresponding to eccentric contraction of the mimicked muscle. The element is also preferably arranged in this manner when the device is utilized to exercise or rehabilitate the muscle that provides movement of the joint in a direction opposite to the mimicked muscle. Of course, the arrangement of the element depends upon the elasticity of the elastic portion.

Preferably, the structure includes a pair of anchors for anchoring the element adjacent opposite ends thereof to respective ones of the body parts forming the joint. The preferred structure further includes a retainer located between the anchors for retaining the element against movement other than linear extension and retraction. If desired, the structure also includes a pliable casing conforming generally to the shape of the joint and adjacent body parts, with the casing, anchors and retainer being attached to one another to form a unitary structure.

The preferred anchors each include a cuff secured about the respective body part. Further, one of the cuffs includes means for tensioning the elastic portion of the mimicking element. The tensioning means preferably includes a buckle assembly adjustably securing a relatively non-elastic strap of the element to the respective body part. The preferred retainer includes a band positioned over the element in the vicinity of the joint so that the element is shiftably disposed between the band and the body.

Other aspects and advantages of the present invention will be apparent from the following detailed description of the preferred embodiments and the accompanying drawing figures.

BRIEF DESCRIPTION OF THE DRAWING FIGURES

A preferred embodiment of the invention is described in detail below with reference to the attached drawing figures, wherein:

FIG. 3 is a right side elevational view of an ankle orthotic constructed in accordance with the principals of the present invention positioned on the ankle joint of a user, particularly illustrating the tissue mimicking element cooperatively secured by the foot and leg anchors, the retainer, and the boot-shaped casing in a mimicking relationship with the peroneus brevis tissue;

FIG. 4 is a left side elevational view of the ankle orthotic shown in FIG. 3, particularly illustrating the reinforcing fabric strip wrapped about the rear side of the joint and secured to the foot anchor cuff adjacent the arch of the foot;

FIG. 5 is a front elevational view of the ankle orthotic shown in FIG. 3, particularly illustrating the lacing for tightening the casing about the ankle joint and adjacent portions of the foot and leg;

FIG. 6 is a rear elevational view of the ankle orthotic shown in FIG. 3;

DETAILED DESCRIPTION OF THE PREFERRED EMBODIMENTS

Figure 1:
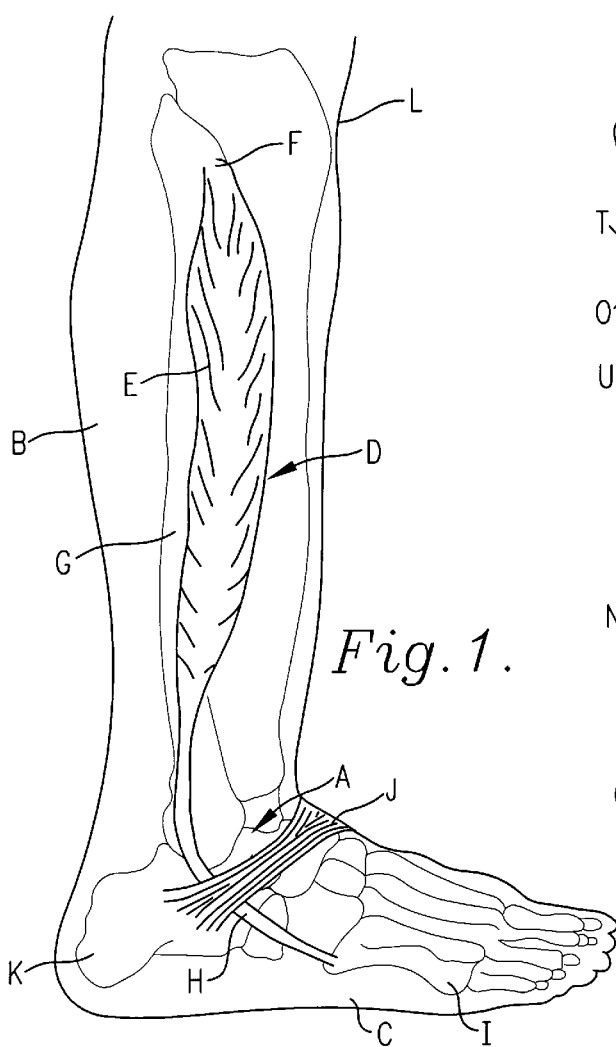
FIG. 1 is a diagrammatic view of the right leg, foot and ankle joint of the human body, particularly illustrating the peroneus brevis tissue extending across the ankle joint and the retinaculum wrapped about the ankle joint for holding the tissue in place during concentric and eccentric contraction of the peroneus brevis muscle.

Turning initially to FIG. 1, the right ankle joint A of the human body is generally formed between the leg B and the foot C. The ankle joint A is flexible in a number of directions including inversion (turning in of the foot), eversion (turning out of the foot), dorsiflexion (turning up of the foot) and plantar flexion (turning down of the foot). Although several hind foot joints permit these movements, the words "ankle joint" as used herein will generally refer to the bone structure which permits up, down, in, or out movement of the foot C relative to the leg B.

Flexion of the ankle joint A is provided by a number of muscles associated with the joint. For example, the peroneus brevis tissue D shown in FIG. 1 provides primarily eversion of the ankle joint A. The peroneus brevis tissue D includes a muscle E, an origin tendon F attaching the muscle E to the fibula G, and a insertion tendon H attaching the muscle to the first metatarsal I of the foot. The peroneus brevis muscle E and tendons F,H collectively extend across the ankle joint A to cooperatively provide, among other movement, eversion of the ankle joint A during concentric contraction of the muscle E. Particularly, the peroneus brevis muscle E shortens during concentric contraction causing linear movement of the insertion tendon H and consequently outward turning of the foot C about the ankle joint A.

The retinaculum J secured to opposite sides of the calcaneus K wraps over the various tissues in the vicinity of the ankle joint A, including the peroneus brevis tissue D, to hold the tissues in place during flexation of the joint. As particularly shown in FIG. 1, the insertion tendon H is shiftably disposed under the retinaculum J so that movement of the tendon H is limited and guided by the retinaculum during concentric and eccentric contraction of the muscle E. That is, the retinaculum J retains the peroneus brevis tissue D against generally all but linear movement across the ankle joint A when the muscle E shortens or extends. The retinaculum J also retains the peroneus brevis tissue D within the confines of the body. In other words, as the peroneus brevis muscle E concentrically contracts, the retinaculum prevents the tissue D from simply shifting outwardly to the shortest distance between the first metatarsal I and the fibula G, which would be located outside the skin layer—the insertion tendon H must shift generally rearwardly under the retinaculum J and then upwardly toward the knee L during concentric contraction of the muscle E.

It will be appreciated that the retinaculum J similarly limits and guides the other tissue associated with the ankle joint A. For example, the retinaculum J retains the tibialis posterior tissue (not shown) extending across the inside of the ankle joint A for providing primarily inversion of the joint. In this respect, during inversion of the ankle joint A, the tibialis posterior muscle (also not shown) concentrically contracts (i.e., shortens) and the peroneus brevis muscle E relaxes (i.e., extends), while eversion of the ankle joint A occurs when the tibialis posterior muscle relaxes (i.e., extends) and the peroneus brevis muscle E concentrically contracts (i.e., shortens). It will also be appreciated that there may be some lateral shifting of the peroneus brevis tissue D during concentric and eccentric contraction of the muscle E because of the natural elasticity and flexibility of the retinaculum J. However, such movement is generally insignificant and is further restricted by the other muscle tissue associated with the ankle joint A.

Of course, there are many joints in the human body, each having certain similarities critical to the present invention. First, each joint of the human body is generally formed between adjacent body parts moveable relative to one another at the joint. Further, at least one tissue, such as the peroneus brevis tissue D shown in FIG. 1, is associated with each joint for providing flexation of the joint. The tissue extends across the joint and includes a muscle and tendons for attaching the muscle to the respective body parts. The tendons and muscle cooperate to flex the joint in a direction or directions during concentric contraction of the muscle (i.e., shortening of the muscle). When the joint extends in an opposite direction or directions the muscle lengthens and eccentrically contracts. Moreover, a retinaculum is provided in the vicinity of the joint for retaining the tissue against substantially all but linear movement.

Figure 2:
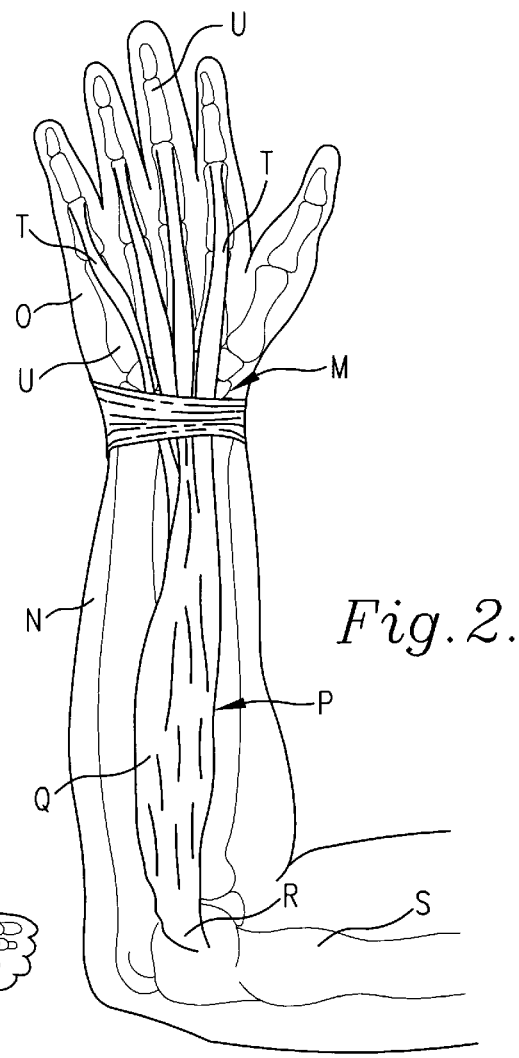
FIG. 2 is a diagrammatic view of the left arm, hand and wrist joint of the human body, particularly illustrating the extensor digitorum tissue extending across the wrist joint and the retinaculum wrapped about the wrist joint for holding the tissue in place during concentric and eccentric contraction of the extensor digitorum muscle.

These similarities are illustrated in FIG. 2, which shows the left wrist joint M formed generally between the arm N and hand O. The extensor digitorum tissue P includes a muscle Q, an origin tendon R attaching the muscle Q to the radial tip of the humerus S, and four insertion tendons T attaching the muscle Q to each of the finger phalanges U. The extensor digitorum muscle Q and tendons R,T collectively extend across the wrist joint M and provide, among other movements, extension of the wrist joint M (i.e., turning up of the hand O) during concentric contraction of the muscle Q. Indeed, the extensor digitorum muscle Q relaxes as the wrist joint M flexes (i.e., as the hand O turns downwardly). Similar to the ankle joint A shown in FIG. 1, the extensor retinaculum V retains the extensor digitorum tissue P against substantially all movement other than linear shortening and extension. Of course, the retinaculum V serves to retain the other tissue for flexing the wrist joint M.

Returning to FIG. 1, a significant number of injuries associated with the ankle joint A involve excessive inversion, which often causes over-extension of the peroneus brevis tissue D and, more particularly, straining of one or both of the tendons F,H. Healing and rehabilitation of such an injury requires that the strained tendon or tendons not be placed under undue stress. It will be appreciated that undue stress of one of the peroneus brevis tendons F or H typically occurs during inversion of the ankle joint A (i.e., during eccentric contraction of the muscle E). The peroneus brevis tendons F,H may likewise be unduly stressed during concentric contraction of the muscle E. Of course, such movement would also unduly stress an injured peroneus brevis muscle.

Turning to FIG. 3, a removable ankle orthotic 10 selected for illustration generally includes an elongated mimicking element 12 and mounting structure, generally referenced by the numeral 14, for mounting the element 12 in a mimicking relationship with the peroneus brevis muscle. In the illustrated embodiment, the mounting structure 14 generally includes a pliable casing 16 conforming to the shape of the ankle joint and the adjacent portions of the leg and foot, a leg anchor 18 for anchoring one end of the element 12 to the leg, a foot anchor 20 for anchoring the opposite end of the element 12 to the foot, and a retainer 22 located between the anchors 16,18 for retaining the element 12 in the vicinity of the ankle joint against substantially all movement other than linear extension and retraction.

The mimicking element 12 includes an elastic cord 24 and a relatively non-elastic strap 26 interconnected by a D-shaped ring 28. Particularly, the cord 24 and strap 26 wrap around the ring and extend toward the leg anchor 18 and foot anchor 20, respectively. The preferred cord 24 is formed of an endless length of rubber tubing, while the strap is preferably formed of nylon fabric. As will be further indicated below, the principals of the present invention are equally applicable to other variously constructed elastic elements.

Turning now to the mounting structure 14, the casing 16 comprises a boot-shaped, tubular sleeve 30 having a heel opening 32 for accommodating the heel of the foot. The illustrated sleeve 30 is formed of a material having sufficient elasticity to apply compression on the ankle joint and adjacent portions of the leg and foot when the sleeve is tightened thereon. The preferred material comprises a laminate of elasticized nylon fabric and neoprene, although other suitable materials such as cloth may be utilized. The sleeve 30 is open along its front and provided with a series of apertures 34 receiving a lace 36 similar to conventional shoe lacing. As perhaps best shown in FIG. 6, a tongue 38 extends across the open front of the sleeve 30 under the lace 36 to prevent chaffing of the leg and foot. Accordingly, the sleeve 30 is tightened about the ankle joint and adjacent portions of the leg and foot by the lace 36 received in the apertures 34. Of course, other suitable means may be utilized to tighten the sleeve 30 on the body, such as straps having hook-and-loop fastening material. It will be appreciated that the compression applied by the casing 16 reduces swelling.

As indicated above, the leg anchor 18 anchors the nylon strap 26 to the outside of the leg. The leg anchor 18 preferably includes an adjustable cuff 40 secured along the backside of the sleeve 30 by suitable stitching 42 (see FIG. 5). The cuff 40 has a loose end 40*a* that threads through a ring 44 (see FIG. 3) and wraps over itself along the front side of the device 10. Suitable fastening structure (not shown) such as a hook-and-loop material (not shown) is provided on the loose end 40*a* for releasibly securing the cuff 40 about the leg. A buckle assembly 46 secured to the cuff 40 adjustably receives a loose end 26*a* of the nylon strap 26. The opposite end of the strap 26 is fixedly secured to the assembly 46 so that the elastic cord 24 is stretched when the loose end 26*a* is pulled by the user. Accordingly, the buckle assembly 46 allows the user to adjust the tension of the elastic cord 24 as necessary. The buckle assembly 46 has a conventional construction, and it should therefore be sufficient to explain that a tab 48 swingably mounted at pivot 50 includes structure (not shown) for frictionally maintaining the nylon strap 26 in a desired position.

The foot anchor 20 similarly includes an adjustable cuff 52 attached medially along the length thereof to the underside of the sleeve 30 by suitable stitching (not shown). The cuff 52 includes a pair of loose ends 52*a* and 52*b* which wrap around the outside and inside of the foot, respectively. As perhaps best shown in FIG. 4, the bottom face of the loose end 52*a* and the top face of the loose end 52*b* have cooperating hook-and-loop material, generally referenced by the numeral 54, for adjustably securing the cuff 52 about the foot. The elastic cord 24 of the mimicking element 12 wraps around a D-shaped ring 56 secured to the outside of the cuff 52 by a fabric loop 58.

The retainer 22 includes a band 60 which cooperates with the sleeve 30 to form a loop through which the elastic cord 24 extends. The band 60 is preferably formed of fabric material and secured at spaced locations to the sleeve 30 by suitable stitching 62 and 64 (see FIG. 3) to form the loop. Similar to the peroneus brevis tissue D and retinaculum J shown in FIG. 1, the band 60 is positioned over the elastic cord 24 in the vicinity of the ankle joint so that the cord 24 is shiftably disposed between the body and the band 60. Accordingly, the band 60 retains the mimicking element 12 against substantially all movement other than linear extension and retraction. Similar to the corresponding structure of the body, there may be slight lateral or outward shifting of the mimicking element 12 because of the elasticity and flexibility of the sleeve 30 and band 60. However, the band 60 includes a elongated reinforcing strip 60*a* for restricting such movement. The strip 60*a* projects from the loop, wraps around the backside of the foot, and is adjustably secured at its loose end to the foot cuff 52 by hook-and-loop fastener material 66 (see FIG. 4). Accordingly, the function of the retainer 22 and the corresponding usages of the word "retain" herein should be interpreted to mean that substantially all movement of the mimicking element 12 is limited to linear extension and retraction, with the understanding that there may be insignificant lateral or outward movement when the element 12 is extended or retracted.

The ankle orthotic 10 may be used a variety of ways. With respect to an injury of the peroneus brevis tissue D shown in FIG. 1, the sleeve 30 is slid onto the body to cover the lower leg B, ankle joint A and foot C. The lace 36 is tied in a suitable manner to tighten the sleeve 30 about the body, whereby the resulting compression applied by the sleeve reduces swelling caused by the injury. The leg cuff 40 and foot cuff 52 are then snugly secured about the leg and foot, respectively. If needed, the tension of the elastic cord 24 is adjusted by pulling the loose end 26*a* of the strap 26 and subsequently securing the strap in the desired arrangement with the buckle assembly 46. Finally, the reinforcing strip 60*a* is tightly wrapped around the backside of the foot and secured to the foot cuff 52. It will be appreciated that the ankle orthotic 10 is functional within various footwear and therefore may be placed within a shoe. These steps may be repeated or performed in a different sequence, if necessary.

With the orthotic 10 placed on the body, the element 12 is retained in a mimicking relationship with the peroneus brevis tissue D. The element 12 is consequently limited to linear movement which corresponds to movement of the mimicked peroneus brevis tissue D. That is, extension of the element 12 corresponds substantially to movement of the mimicked peroneus brevis muscle E and tendons F, H during relaxation or eccentric contraction (i.e., extension) of the muscle E, and retraction of the element 12 corresponds substantially to movement of the mimicked muscle E and tendons F, H during concentric contraction (i.e., shortening) of the muscle E.

During the acute stage of an injury to the tissue, the elastic cord 24 may be significantly tensioned so that inversion of the ankle joint, and therefore extension of the tissue D, is prevented. However, the tensioned element 12 does not restrict other flexation of the ankle joint so that the ankle orthotic is not overly restrictive. If necessary, a mimicking element may also be mounted in a mimicking relationship with the tibialis posterior muscle along the opposite side of the mounting structure 14 so that eversion of the ankle joint is also prevented. Indeed, such an arrangement would virtually immobilize the ankle joint.

During rehabilitation of the injured peroneus brevis tissue D, the tension of the elastic cord 24 is progressively reduced as the tissue heals. Accordingly, the freedom of the ankle joint to move in directions corresponding to eccentric contraction of the peroneus brevis muscle depends upon the tension of the elastic cord 24. At some point during the rehabilitation stage, the tension of the element 12 will have sufficiently decreased to allow limited inversion of the ankle joint. However, such movement is limited by the expandability of the tensioned elastic cord 24 so that the corresponding extension of the peroneus brevis tissue does not place undue stress on the injured muscle or tendon. Further, the tensioned elastic cord 24 urges eversion of the ankle joint so as to supplement the peroneus brevis tissue during concentric contraction of the peroneus brevis muscle. Accordingly, the peroneus brevis tissue is not unduly stressed during ankle joint movement corresponding to concentric and eccentric contraction of the peroneus brevis muscle.

It will be appreciated that the ankle orthotic 10 has also proven useful in treating sprained ligaments. During both the acute and rehabilitative stages of an injury the mimicking element 12 may be arranged to relieve stress on injured ligaments. For example, the elastic cord 24 may be tensioned so that the ankle joint is slightly everted whereby tension in the posterior talofibular, calcaneofibular, and anterior talofibular ligaments is reduced and over-stretching of the same is prevented.

Once the injured peroneus brevis tissue D has healed, the ankle orthotic 10 may also be used as a prophylaxis to reduce the risk of re-injury. Preferably, the elastic cord 24 is under slight tension when the ankle joint is in a neutral position (i.e., when the ankle joint is neither inverted or everted). Accordingly, the mimicking element 12 supplements the peroneus brevis tissue D during concentric contraction of the peroneus brevis muscle and limits extension of the tissue during inversion of the ankle joint. Of course, the elastic cord 24 may be further tensioned when the orthotic 10 is utilized as a prophylaxis should there be a risk of injury when the peroneus brevis tissue concentrically contracts.

The ankle orthotic 10 may also be utilized to exercise the tissues that flex the ankle joint in a direction or directions opposite to the flexation provided by the peroneus brevis tissue. For example, when the mimicking element 12 is arranged in a manner similar to the prophylaxis application described above, the tibialis posterior muscle must work against the elastic cord 24 to invert the ankle joint. That is, the elastic cord 24 resists inversion of the ankle joint and thereby exercises the tibialis posterior tissue. It may also be useful to exercise a tissue during the rehabilitation stage of an injury. Accordingly, the mimicking element 12 may be routinely removed or loosened while an element (not shown) is mounted in a mimicking relationship with the tibialis posterior tissue during rehabilitation of the peroneus brevis tissue.

In view of the foregoing, FIGS. 3–6 illustrate a removable ankle orthotic 10 which focuses on the peroneus brevis tissue. In other words, the ankle orthotic 10 is particularly configured to treat an injury to the peroneus brevis tissue, reduce the risk of re-injury to the peroneus brevis tissue, or exercise muscles that flex the ankle joint in a direction or directions opposite to the flexation provided by the peroneus brevis tissue. However, the mounting structure 14 may be constructed to mount the element 12 in a mimicking relationship with one of the other tissues associated with the ankle joint. As indicated above, the mimicking element may be mounted along the inside of the lower leg, ankle joint and foot to mimic the tibialis posterior tissue. Further, the leg anchor 18, foot anchor 20 and/or retainer 22 may be designed for selective movement about the ankle joint. For example, the outer surfaces of the leg cuff 40 and foot cuff 52 and the inner surfaces of the buckle assembly 46 and fabric loop 58 may be provided with a releasable fastening material, such as hook-and-loop material, so that the anchor points may be variously arranged about the ankle joint. The outer surface of the sleeve 24 and the band 60 may similarly be provided with releasable fastening material to allow placement of the band in various locations in the vicinity of the ankle joint.

The principals of the present invention are equally applicable to other constructional variations of the ankle orthotic 10. For example, the casing 16 may be eliminated, whereby only the leg cuff 40 and foot cuff 52 anchor the opposite ends of the mimicking element 12 to the leg and foot, respectively. With this embodiment, the retainer would most likely have to be secured to the heel in some manner (e.g., by a heel cuff or cup). Alternatively, the leg and foot cuffs 40 and 52 may be eliminated so that the buckle assembly 46 and fabric loop 58 are secured directly to the sleeve 30. This would most likely require the sleeve to be formed of a more rigid material. The construction of the mimicking element 12 may also be varied. For example, a plurality of alternately selectable mimicking elements may be removably anchored to the leg and foot, each element being formed of the same material and having a different length or width, or being formed of different materials having different elasticities. Accordingly, one of the elements is selected for use with the mounting structure depending upon the desired application. The elements may be color-coded to facilitate the use thereof.

Figure 7:
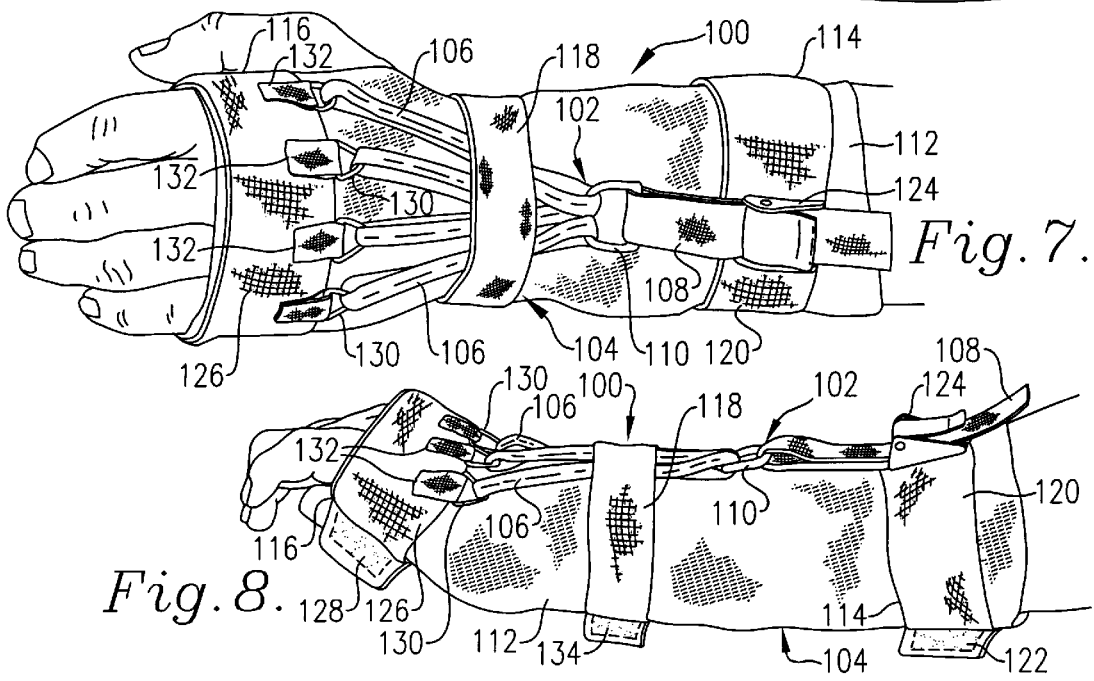
FIG. 7 is a top elevational view of an alternative embodiment constructed as a wrist orthotic, particularly illustrating the orthotic positioned on the wrist joint of a user, with the tissue mimicking element cooperatively secured by the hand and arm anchors, the retainer, and the casing in a mimicking relationship with the extensor digitorum tissue.
Figure 8:
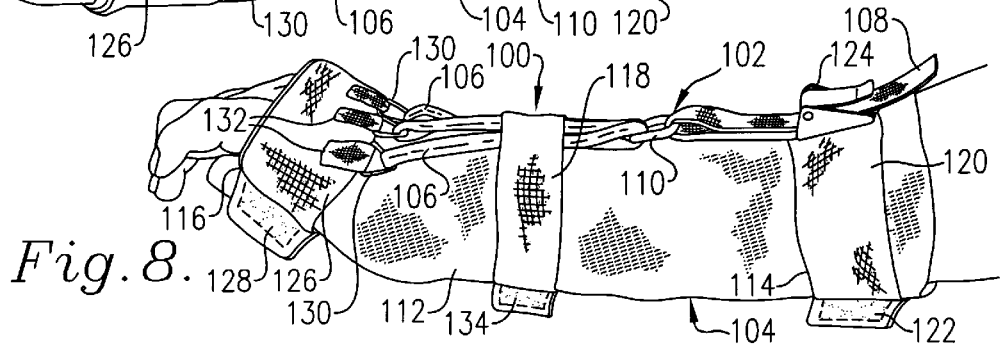
FIG. 8 is a left side elevational view of the wrist orthotic shown in FIG. 7, particularly illustrating the elastic portion of the mimicking element being sufficiently tensioned to dispose the hand in a "cocked up" position.

Moreover, it is entirely within the ambit of the present invention to provide an orthotic device for mimicking one or more of the muscles associated with another joint of the human body. For example, FIGS. 7–8 illustrate a removable wrist orthotic 100 constructed in accordance with the principals of the present invention. The construction of the wrist orthotic is similar in many respects to the ankle orthotic 10 shown in FIGS. 3–6 and therefore will not be described in with the same detail herein. Accordingly, suffice to explain that the wrist orthotic 100 generally includes a mimicking element 102 and mounting structure, broadly referenced by the numeral 104, for mounting the element 102 in a mimicking relationship with the extensor digitorum tissue (referenced by the letter P in FIG. 2).

The mimicking element 102 includes four elastic cords 106 each preferably formed of an endless length of rubber tubing and connected to a relatively non-elastic nylon strap 108 by a D-shaped ring 110. The cords 106 are arranged along the top of the hand and wrist in a manner similar to the insertion tendons of the extensor digitorum tissue (compare FIGS. 2 and 7).

The mounting structure 104 generally includes a pliable sleeve 112 formed of elastic material, an arm anchor 114 for anchoring the nylon strap 108 to the arm, a hand anchor 116 for anchoring the elastic cords 106 to the hand, and a retainer 118 for retaining the element 102 against substantially all movement other than linear extension and retraction. The arm anchor includes a cuff 120 releasably secured about the arm by hook-and-loop fastening material 122 and a buckle assembly 124 for allowing adjustment of the tension of the elastic cords 106. The hand anchor 116 similarly includes a cuff 126 releasably secured about the hand by hook-and-loop material 128. Each elastic cord 106 is coupled with a ring 130 secured to the top surface of the cuff 126 by a fabric loop 132. The retainer 118 comprises a band of material positioned over the elastic cords 106 in the vicinity of the wrist joint, with the band being releasably secured about the body with hook-and-loop material 134. The cuffs 120,126 and retainer band 118 are preferably attached to the pliable sleeve 112 by suitable stitching (not shown).

As shown in FIGS. 7–8, the elastic cords 106 have been stretched (i.e., the cords are under tension) so that the hand is disposed in a "cocked up" position. Accordingly, the mimicking element 102 restricts flexion of the wrist joint so as to avoid over-extension of the extensor digitorum tissue. Of course, the wrist orthotic 100 may also be used in the other various applications noted above with respect to the ankle orthotic 10.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. An orthotic device for a joint formed between adjacent human body parts, wherein the joint is flexed by tissue extending across the joint, said device comprising:

an elongated element having at least a portion thereof that is elastic, such that the elongated element is resiliently extendable; and structure operable to mount the element on the body so that the element extends across the joint in a mimicking relationship with the tissue, said structure including a pair of anchors operable to anchor the element to respective ones of the body, parts, and a retainer located between the anchors and configured to prevent substantially all movement of the element in the vicinity of the joint other than generally longitudinal shifting of the element relative to the retainer, said retainer presenting a pair of opposed side margins defining therebetween a width and overlying a portion of said elongated element and presenting through passageway extending the entire width of said retainer between said opposed side margins, said element extending through said passageway and being longitudinally shiftable relative to the retainer.

2. An orthotic device as claimed in claim 1, said element including an elastic portion and a relatively non-elastic portion interconnected with the elastic portion.

3. An orthotic device as claimed in claim 2, said elastic portion comprising a plurality of elongated cords, each being connected to the non-elastic portion.

4. An orthotic device as claimed in claim 2, said elastic portion comprising an elongated cord.

5. An orthotic device as claimed in claim 4, said cord being formed of a length of rubber tubing.

6. An orthotic device as claimed in claim 4, said non-elastic portion including a nylon strap, and a ring about which the strap and the cord are wrapped for interconnecting the elastic and non-elastic portions.

7. An orthotic device as claimed in claim 1, said structure being configured to support the element in tension for reducing the risk of over-extension of the tissue and for supplementing the tissue.

8. An orthotic device as claimed in claim 1, one of said anchors including tensioning means for adjusting the tension of the element.

9. An orthotic device as claimed in claim 8, said element including a relatively non-elastic strap, said element tensioning means including a buckle assembly for adjustably securing the strap to the respective body part.

10. An orthotic device as claimed in claim 8, said anchors each including a cuff configured to be releasably secured about the respective body part.

11. An orthotic device for a joint formed between adjacent human body parts, wherein the joint is flexed by tissue extending across the joint, said device comprising:

an elongated element including an elastic portion; and structure operable to mount the element on the body so that the element extends across the joint in a mimicking relationship with the tissue, said structure including a pair of anchors operable to anchor the element to respective ones of the body parts, and a retainer located between the anchors and configured to prevent substantially all movement of the element in the vicinity of the joint other than generally longitudinal shifting of the element relative to the retainer, said retainer presenting a pair of opposed side margins defining therebetween a width and overlying a portion of said elongated element and presenting a through passageway extending the entire width of said retainer between said opposed side margins, said element extending through said passageway and being longitudinally shiftable relative to the retainer, one of said anchors including tensioning means for adjusting the tension of the elastic portion, said anchors each including a cuff configured to be releasably secured about the respective body part, said retainer including a band positioned over the element in the vicinity of the joint so that the element is shiftably disposed between the body and the band.

12. An orthotic device as claimed in claim 11, said band being configured for wrapping around the body in the vicinity of the joint.

13. An orthotic device as claimed in claim 11, said structure including a pliable casing conforming generally to the shape of the joint and adjacent body parts for removable placement thereon, said band being secured to the casing in the vicinity of the joint in a manner to form a loop that defines the passageway through which the element extends.

14. An orthotic device as claimed in claim 13, said band including a reinforcing portion for assisting with retaining the element against movement other than linear extension and retraction.

15. An orthotic device as claimed in claim 14, said reinforcing portion comprising an elongated fabric strip projecting adjacent one end from the loop and releasably secured adjacent an opposite end to the casing disposed along a side of the joint opposite from the loop.

16. An orthotic device as claimed in claim 1, said anchors each including a cuff configured to be releasably secured about the respective body part.

17. An orthotic device for a joint formed between adjacent human body parts, wherein the joint is flexed by tissue extending across the joint, said device comprising:

an elongated element including an elastic portion; and structure operable to mount the element on the body so that the element extends across the joint in a mimicking relationship with the tissue, said structure including a pair of anchors operable to anchor the element to respective ones of the body parts, and a retainer located between the anchors and configured to prevent substantially all movement of the element in the vicinity of the joint other than generally longitudinal shifting of the element relative to the retainer, said retainer presenting a pair of opposed side margins defining therebetween a width and overlying a portion of said elongated element and presenting a through passageway extending the entire width of said retainer between said opposed side margins, said element extending through said passageway and being longitudinally shiftable relative to the retainer, said retainer including a band positioned over the element in the vicinity of the joint so that the element is shiftably disposed between the body and the band.

18. An orthotic device as claimed in claim 17, said band being configured for wrapping around the body in the vicinity of the joint.

19. An orthotic device as claimed in claim 17, said structure including a pliable casing conforming generally to the shape of the joint and adjacent body parts for removable placement thereon, said band being secured to the casing in the vicinity of the joint in a manner to form a loop that defines the passageway through which the element extends.

20. An orthotic device as claimed in claim 19, said band including a reinforcing portion for assisting with retaining the element against movement other than linear extension and retraction, said reinforcing portion comprising an elongated fabric strip projecting adjacent one end from the loop and releasably secured adjacent an opposite end to the casing disposed along a side of the joint opposite from the loop.

21. An orthotic device as claimed in claim 1, said structure including a pliable casing conforming generally to the shape of the joint and adjacent body parts for removable placement thereon.

22. An orthotic device as claimed in claim 21, said casing, anchors, and retainer being attached to one another and thereby forming a unitary structure for removable placement on the body.

23. An orthotic device as claimed in claim 22, said casing comprising an elastic tubular sleeve for receiving the joint and adjacent body parts, and means for tightening the sleeve about the body.

24. An ankle orthotic comprising:

an elongated element having at least a portion thereof that is elastic, such that the elongated element is resiliently extendable; and structure for securing the element on the body to extend across the ankle in a mimicking relationship with one of the muscles and the associated tendons collectively extending a cross the ankle, said structure including a leg anchor for anchoring the element adjacent one end thereof to the leg, a foot anchor for anchoring the element adjacent an opposite end thereof to the foot, and a retainer located between the anchors and configured to prevent substantially all movement of the element in the vicinity of the ankle joint other than generally longitudinal shifting of the element relative to the retainer, said retainer presenting a pair of opposed side margins defining therebetween a width and overlying a portion of said elongated element and presenting a through passageway extending the entire width of said retainer between said opposed side margins, said element extending through said passageway and being longitudinally shiftable relative to the retainer.

25. An ankle orthotic as claimed in claim 24, said element including an elastic portion and a relatively non-elastic portion interconnected with the elastic portion.

26. An ankle orthotic as claimed in claim 25, said elastic portion comprising an elongated cord formed of a length of rubber tubing.

27. An ankle orthotic as claimed in claim 26, said non-elastic portion including a nylon strap, and a ring about which the strap and the cord are wrapped for interconnecting the elastic and non-elastic portions.

28. An ankle orthotic as claimed in claim 24, said leg anchor or said foot anchor including tensioning means for adjusting the tension of the element.

29. An ankle orthotic as claimed in claim 28, said element including a relatively non-elastic strap, said element tensioning means including a buckle assembly for adjustably securing the strap to the leg or foot.

30. An ankle orthotic as claimed in claim 28, said leg anchor including a leg cuff configured to be releasably secured about the leg, and said foot anchor including a foot cuff configured to be releasably secured about the foot.

31. An ankle orthotic comprising:

an elongated element including an elastic portion; and structure for securing the element on the body to extend across the ankle in a mimicking relationship with one of the muscles and the associated tendons collectively extending across the ankle, said stricture including a leg anchor for anchoring the element adjacent one end thereof to the leg, a foot anchor for anchoring the element adjacent an opposite end thereof to the foot, and a retainer located between the anchors and configured to prevent substantially all movement of the element in the vicinity of the ankle joint other than generally longitudinal shifting of the element relative to the retainer, said retainer presenting a pair of opposed side margins defining there between a width and overlying a portion of said elongated element and presenting a through passageway extending the entire width of said retainer between said opposed side margins, said element extending through said passageway and being longitudinally shiftable relative to the retainer, said leg anchor or said foot anchor including tensioning means for adjusting the tension of the elastic portion, said leg anchor including a leg cuff configured to be releasably secured about the leg, and said foot anchor including a foot cuff configured to be releasably secured about the foot, said structure including a pliable casing conforming generally to the shape of the ankle and adjacent portions of the leg and foot for removable placement thereon, said retainer including a band secured to the casing in the vicinity of the ankle in a manner to form a loop that defines the passageway through which the element extends.

32. An ankle orthotic as claimed in claim 31, said band including a reinforcing portion for assisting with retaining the element against movement other than linear extension and retraction, said reinforcing portion comprising an elongated fabric strip projecting adjacent one end from the loop and releasably secured adjacent an opposite end to the casing disposed along a side of the ankle opposite from the loop.

33. An ankle orthotic as claimed in claim 29, said leg anchor including a leg cuff configured to be releasably secured about the leg, and said foot anchor including a foot cuff configured to be releasably secured about the foot.

34. An ankle orthotic comprising
an elongated element including an elastic portion; and
structure for securing the element on the body to extend across the ankle in a mimicking relationship with one of the muscles and the associated tendons collectively extending across the ankle,
said structure including a leg anchor for anchoring the element adjacent one end thereof to the leg, a foot anchor for anchoring the element adjacent an opposite end thereof to the foot, and a retainer located between the anchors and configured to prevent substantially all movement of the clement in the vicinity of the ankle joint other than generally longitudinal shifting of the element relative to the retainer,
said retainer presenting a pair of opposed side margins defining therebetween a width and overlying a portion of said elongated element and presenting a though passageway extending the entire width of said retainer between said opposed side margins,
said element extending through said passageway and being longitudinally shiftable relative to the retainer,
said retainer including a band positioned over the element in the vicinity of the ankle so that the element is shiftably disposed between the body and the band.

35. An ankle orthotic as claimed in claim 34,
said structure including a pliable casing conforming generally to the shape of the ankle and adjacent portions of the leg and foot for removable placement thereon,
said band being secured to the casing in the vicinity of the ankle in a manner to form a loop that defines the passageway through which the element extends.

36. An ankle orthotic as claimed in claim 35,
said band including a reinforcing portion for assisting with retaining the element against movement other than linear extension and retraction.

37. An ankle orthotic as claimed in claim 36,
said reinforcing portion comprising an elongated fabric strip projecting adjacent one end from the loop and releasably secured adjacent an opposite end to the casing disposed along a side of the ankle opposite from the loop.

38. An ankle orthotic as claimed in claim 24,
said structure including a pliable casing conforming generally to the shape of the ankle and adjacent portions of the leg and foot for removable placement thereon,
said casing, anchors, and retainer being attached to one another and thereby forming a unitary structure.

39. An ankle orthotic as claimed in claim 38,
said casing comprising an elastic boot-shaped sleeve for receiving the ankle and adjacent portions of the leg and foot, and means for tightening the sleeve about the body.

40. A wrist orthotic comprising:
an elongated element having at least a portion thereof that is elastic, such that the elongated element is resiliently extendable; and
structure for securing the element on the body to extend across the wrist in a mimicking relationship with one of the muscles and the associated tendons collectively extending across the wrist,
said structure including an arm anchor for anchoring the element adjacent one end thereof to the arm, a hand anchor for anchoring the element adjacent an opposite end thereof to the hand, and a retainer located between the anchors and configured to prevent substantially all movement of the element in the vicinity of the wrist joint other than generally longitudinal shifting of the element relative to the retainer,
said retainer presenting a pair of opposed side margins defining therebetween a width and overlying a portion of said elongated element and presenting a through passageway extending the entire width of said retainer between said opposed side margins,
said element extending through said passageway and being longitudinally shiftable relative to the retainer.

41. A wrist orthotic as claimed in claim 40,
said clement including an elastic portion and a relatively non-elastic portion interconnected with the elastic portion.

42. A wrist orthotic as claimed in claim 41,
said elastic portion comprising a plurality of elongated cords, each comprising a length of rubber tubing and being connected to the non-elastic portion.

43. A wrist orthotic as claimed in claim 42,
said non-elastic portion including a nylon strap, and a ring about which the strap and the cords are wrapped for interconnecting the elastic and non-elastic portions.

44. A wrist orthotic as claimed in claim 40,
said arm anchor or said hand anchor including tensioning means for adjusting the tension of the element.

45. A wrist orthotic as claimed in claim 44,
said element including a relatively non-elastic strap,
said element tensioning means including a buckle assembly for adjustably securing the strap to the arm or hand.

46. A wrist orthotic as claimed in claim 44,
said arm anchor including an arm cuff configured to be releasably secured about the arm, and
said hand anchor including a hand cuff configured to be releasably secured about the hand.

47. A wrist orthotic as claimed in claim 46,
said retainer including a band positioned over the element in the vicinity of the wrist so that the element is shiftably disposed between the body and the band.

48. A wrist orthotic as claimed in claim 47,
said band being configured for wrapping around the body in the vicinity of the wrist.

49. A wrist orthotic as claimed in claim 48,
said structure including a pliable casing conforming generally to the shape of the wrist and adjacent portions of the arm and hand for removable placement thereon.

50. A wrist orthotic as claimed in claim 40,
said arm anchor including an arm cuff configured to be releasably secured about the arm, and
said hand anchor including a hand cuff configured to be releasably secured about the hand.

51. A wrist orthotic as claimed in claim 40,
said retainer including a band positioned over the element in the vicinity of the wrist so that the element is shiftably disposed between the body and the band.

52. A wrist orthotic as claimed in claim 51,
said band being configured for wrapping around the body in the vicinity of the wrist.

53. A wrist orthotic as claimed in claim 40,
said structure including a pliable sleeve conforming generally to the shape of the wrist and adjacent portions of the arm and hand for removable placement thereon,
said casing, anchors, and retainer being attached to one another and thereby forming a unitary structure for removable placement on the body.

* * * * *